(12) United States Patent
Leung

(10) Patent No.: US 11,224,860 B2
(45) Date of Patent: Jan. 18, 2022

(54) NANOFIBER SURFACES

(71) Applicant: The Hong Kong Polytechnic University, Hong Kong (HK)

(72) Inventor: Woon-Fong Wallace Leung, Hong Kong (HK)

(73) Assignee: The Hong Kong Polytechnic University, Hong Kong (HK)

(*) Notice: Subject to any disclaimer, the term of this patent is extended or adjusted under 35 U.S.C. 154(b) by 0 days.

(21) Appl. No.: 16/288,860

(22) Filed: Feb. 28, 2019

(65) Prior Publication Data

US 2020/0276560 A1  Sep. 3, 2020

(51) Int. Cl.
 *B01J 35/06* (2006.01)
 *B01J 37/00* (2006.01)
 *B01J 23/18* (2006.01)
 *B01J 21/06* (2006.01)
 *B01J 35/00* (2006.01)
 (Continued)

(52) U.S. Cl.
 CPC .......... *B01J 23/18* (2013.01); *B01D 53/8628* (2013.01); *B01D 53/8668* (2013.01); *B01J 21/063* (2013.01); *B01J 21/16* (2013.01); *B01J 27/232* (2013.01); *B01J 35/004* (2013.01); *B01J 35/06* (2013.01); *B01J 37/0018* (2013.01); *B01J 37/0219* (2013.01); *B01D 2255/20707* (2013.01); *B01D 2255/802* (2013.01); *B01D 2257/404* (2013.01); *B01D 2257/708* (2013.01)

(58) Field of Classification Search
 CPC . B01J 23/18; B01J 21/16; B01J 21/063; B01J 35/004; B01J 37/0219; B01J 37/0018; B01J 27/232; B01J 35/06; B01D 53/8628; B01D 53/8668; B01D 2255/802; B01D 2257/708; B01D 2255/20707; B01D 2257/404
 USPC ......................................................... 422/121
 See application file for complete search history.

(56) References Cited

U.S. PATENT DOCUMENTS 6,228,480 B1 * 5/2001 Kimura .................. B01J 35/002
                                                      106/287.13
7,208,443 B1 * 4/2007 Kimura .................. B32B 15/08
                                                      502/232
(Continued)

FOREIGN PATENT DOCUMENTS

CN        1805790 A        7/2006
CN        1901994 A        1/2007
(Continued)

OTHER PUBLICATIONS

Carina Chun Pei, Kenneth Kim Shing Lo, Wallace Woon-Fong Leung. Titanium-Zin-Bismuch oxides-graphene composite nanofibers as high-performance photocatalyst for gas purification. Separation and Purification Technology 184 (2017) 205-212 (Year: 2017).*
(Continued)

*Primary Examiner* — Huy Tram Nguyen
(74) *Attorney, Agent, or Firm* — Mintz, Levin, Cohn, Ferris, Glovsky and Popeo, P.C.; Steven M. Jensen; Joohee Lee

(57) ABSTRACT

The present disclosure relates to a surface comprising a photocatalyst affixed thereupon via an adhesive layer and methods for affixing the photocatalyst to the surface via the adhesive layer. The present disclosure also provides a purifier comprising the photocatalyst affixed surface and a purifier system comprising such purifier.

19 Claims, 14 Drawing Sheets

(51) Int. Cl.
*B01J 27/232* (2006.01)
*B01J 21/16* (2006.01)
*B01D 53/86* (2006.01)
*B01J 37/02* (2006.01)

(56) References Cited

U.S. PATENT DOCUMENTS

| | | | | |
|---|---|---|---|---|
| 7,910,513 | B2* | 3/2011 | Toyoda | B32B 27/18 |
| | | | | 502/208 |
| 2004/0024108 | A1* | 2/2004 | Sugihara | C01G 23/08 |
| | | | | 524/497 |
| 2011/0183571 | A1 | 7/2011 | Lombardi | |
| 2014/0158986 | A1* | 6/2014 | Leung | B82Y 10/00 |
| | | | | 257/26 |
| 2015/0266013 | A1* | 9/2015 | Leung | B01J 19/127 |
| | | | | 204/157.3 |
| 2018/0361363 | A1* | 12/2018 | Kobayashi | C01B 3/04 |

FOREIGN PATENT DOCUMENTS

| | | |
|---|---|---|
| CN | 201062308 Y | 5/2008 |
| CN | 102358964 A | 2/2012 |
| CN | 103184685 A | 7/2013 |
| CN | 104099725 A | 10/2014 |
| CN | 104553174 A | 4/2015 |
| CN | 104862965 A | 8/2015 |
| CN | 108026691 A | 5/2018 |
| JP | 2018-145558 A | 9/2018 |
| WO | 2008/131642 A1 | 11/2008 |
| WO | WO-2017145707 A1 * 8/2017 ......... C01B 13/0207 |

OTHER PUBLICATIONS

Pei, C.C. et al., "Photocatalytic degradation of Rhodamine B by $TiO_2/ZnO$ nanofibers under visible-light irradiation", Separation and Purification Technology, 114 (2013) 108-116, DOI:1016/j.seppur.2013.04.032, 2013.
International Search Report for International Patent Application No. PCT/CN2020/073363, dated Apr. 20, 2020, 6 pages.
Alkyd, web pages retreived from Wikipedia on May 14, 2021, https://en.wikipedia.org/w/index.php?title=Alkyd&oldid=1017490804.
Alkyd resin, web pages retrieved on May 14, 2021 from Britannica, https://www.britannica.com/print/article/15764.
Alkyd resin—CAMEO, web pages retrieved on May 14, 2021, http://cameo.mfa.org/wiki/Alkyd.
Vegetable oil based eco-friendly coating materials: A review article, Manawwer et al, Arbian Journal of Chemistry (2014) 7, 469-479.
Exhibit A: Production Data; Camel Professional Synthetic Enamel CM Series.
Exhibit B: Soucek et al., "Alkyd Resin Synthesis", Encyclopedia of Polymeric Nanomaterials, first published online: Dec. 2, 2014, DOI: https://doi.org/10.1007/978-3-642-36199-9_278-1.
Exhibit C: Correspondence from W. Leung to J. McLean on Apr. 29, 2021 regarding Inquiry about Camel Professional Synthetic Enamel 1800 Series.

* cited by examiner

NANOFIBER SURFACES

TECHNICAL FIELD

The present disclosure relates to surfaces with nanofibres affixed thereto.

BACKGROUND

Photocatalysts are substances which can modify the rate of a chemical reaction using energy from light irradiation. Photocatalysts, such as titanium dioxide ($TiO_2$), have been widely used in various environmental and energy applications, including self-cleaning surfaces, air and water purification systems, sterilization, hydrogen evolution, and photoelectrochemical conversion.

Photocatalysts' performance can benefit greatly when they take form of nanostructures that increase the surface area for adsorption of gas molecules, harvesting of light, and fostering of the chemical reaction of the superanions and hydroxyl radicals with the gas molecules adsorbed on the photocatalyst surface. The superanions and hydroxyl radicals are generated from the photogenerated electrons and the left-behind positive holes with the oxygen and water moisture in air, respectively. Similar reactions can be also found in water as well. For example, photocatalyst, $TiO_2$ is commercially available as a $TiO_2$ P25 nanoparticle with average primary particle size 21±5 nm, although larger particles of $TiO_2$, such as 200 nm, have also been commonly used.

For the purpose of water purification, these heterogeneous nanoparticles are generally mixed with the water to be purified. After the organic pollutants in water are broken down by the photochemical reaction, the heterogeneous catalysts are separated from the aqueous solution and may be recycled. However, loss of catalyst during separation and recycling are inevitable. Further loss may also occur in washing the catalyst, which is required to remove any unwanted organic substance absorbed on the surface of the catalyst that might impair its function. The loss of nanoparticles in the water may cause problems if the water is to be filtered and purified for reuse. Even if the wastewater is to be disposed of, it is undesirable to dispose wastewater with nanoparticles due to impact of nanomaterials on the environment.

For air purification, $TiO_2$, nanoparticles may be in form of a liquid suspension which is then sprayed onto walls of a room or space. After the liquid is evaporated, the $TiO_2$ nanoparticles on the walls harvest the light in the room and combine with oxygen or water moisture in air to form respectively super-anions, $O_2^-$, or hydroxyl radicals, $OH^-$. These super-anions and hydroxyl radicals can oxidize harmful gas molecules adsorbed onto the surface of the $TiO_2$ particles. However, there is a concern that the $TiO_2$ nanoparticles may be detached and get inhaled by occupants in the rooms, which is equally undesirable as inhaling air with harmful gases.

Another constraint with $TiO_2$ nanoparticles is that they can typically only harvest ultraviolet (UV) light, which a person skilled in the art would appreciate is only 5% of the light spectrum.

As such, there is a need to provide photocatalyst that at least alleviates or ameliorates one or more of the above problems.

SUMMARY

Features and advantages of the disclosure will be set forth in the description which follows, and in part will be obvious from the description, or can be learned by practice of the herein disclosed principles. The features and advantages of the disclosure can be realized and obtained by means of the instruments and combinations specified in the appended claims.

In accordance with a first aspect of the present disclosure, there is provided a surface comprising a photocatalyst affixed thereupon via an adhesive layer.

Optionally, the photocatalyst may be affixed via an adhesive layer comprising an oil-based paint.

Preferably, the photocatalyst comprises $TiO_2$, $TiO_2$—ZnO, $TiO_2$—$Bi_2O_3$, $TiO_2$—CuO, $TiO_2$—CuO-Gr, $TiO_2$—ZnO—$Bi_2O_3$ or $TiO_2$—ZnO—$Bi_2O_3$-Gr.

Advantageously, the photocatalyst is $TiO_2$—ZnO, $TiO_2$—$Bi_2O_3$, $TiO_2$—CuO, $TiO_2$—CuO-Gr, $TiO_2$—ZnO—$Bi_2O_3$ or $TiO_2$—ZnO—$Bi_2O_3$-Gr nanofiber or nanohair.

More advantageously, the photocatalyst is $TiO_2$—ZnO—$Bi_2O_3$-Gr nanofiber or truncated nanofiber (nanohair).

The oil-based paint may comprise a white pigment, and the white pigment may be calcium carbonate, kaolin or titanium dioxide.

Preferably, the adhesive layer is permeable to light and gas. More preferably, the adhesive layer is permeable to water vapor.

The photocatalyst may also be affixed via thermal treatment of an adhesive layer having the photocatalyst thereupon.

According to another aspect of the disclosure there is provided a method of affixing a photocatalyst to a surface comprising applying a suspension of the photocatalyst in an oil-based paint to the surface.

In yet a further aspect of the disclosure there is provided a purifier comprising a photocatalyst affixed on a surface via an adhesive layer wherein the adhesive layer comprises $TiO_2$.

Preferably, the adhesive layer has a composition substantially the same as the photocatalyst.

Advantageously, the adhesive layer has a composition at least 99%, 98%, 90%, 80%, 70%, 60%, 50%, 40%, 30%, 20% or 10% similar with the photocatalyst.

More advantageously, the adhesive layer is permeable to gas and water vapor.

In a further aspect of the disclosure there is provided an air purifier system comprising an inlet in fluid communication with an outlet, and a purifier disposed on a fluid path from the inlet to the outlet, wherein the purifier comprising a photocatalyst affixed on a surface via an adhesive layer and wherein the adhesive layer comprises $TiO_2$.

The photocatalyst may be affixed proximal to the intake surface or output surface of the fluid path or on any surface along the fluid path.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings.

Preferred embodiments of the present invention will be explained in further detail below by way of examples and with reference to the accompanying drawings, in which:—

DETAILED DESCRIPTION OF THE PREFERRED EMBODIMENTS

Various embodiments of the disclosure are discussed in detail below. While specific implementations are discussed, it should be understood that this is for illustration purposes only. A person skilled in the relevant art will recognize that other components and configurations may be used without departing from the spirit and scope of the disclosure.

Figure 1:
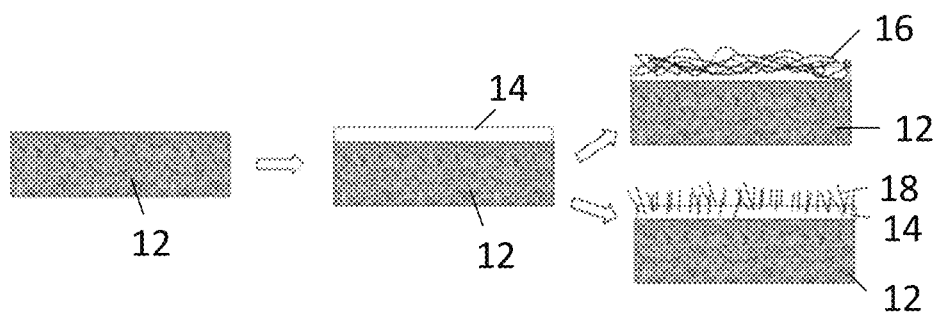
FIG. 1 shows a schematic illustration of a first aspect of the present disclosure wherein a coating of nanofibers or nanohairs are attached onto grains of a porous media via an adhesive layer using a sol-gel process.

Referring to FIG. 1, there is shown a first aspect of the present disclosure in which nanofibers 16 or truncated nanofibres 18 are coated on the surfaces of a porous media 12 via an adhesive layer 14 using a sol-gel method. The adhesive layer 14 is selected from semiconductor materials (e.g. TiO2 particles) having a composition similar to that of the nanofibers or nanohair photocatalyst. The adhesive layer 14 is applied to surface of the porous media 12 via say a tool such as a doctor's knife in an ultrathin layer. Then, nanofibres 16 and/or nanohairs 18 are applied to the adhesive layer 14. The resulting structure is calcinated optimally at 450 degree Celsius. Upon calcination the nanofibres 16 and nanohairs 18 are fused into the adhesive layer 14 which is attached to the surface of the porous media 12. The porous media 12 may be formed by grains of similar size or different sizes filling a container that has transparent wall allowing light to transmit through activating the contained photocatalytic nanofibers/nanohairs coated on the grains. The porous media may also be a ceramic filter, coated with photocatalyst onto the surface, in a transparent housing; or alternatively in a combination of both geometries.

Optionally, the adhesive layer 14 may be an oil based paint as is discussed in further detail below; or may be another thin porous adhesive layer, which advantageously affixes the nanofibers or nanohairs to the porous surface with sufficient attachment, yet allow both gaseous molecules and light to permeate through to the embedded photocatalyst nanofibers upon curing of the adhesive layer so as to resist shear forces from cleaning (indoor) or rain (outdoor).

As used herein, the term Nanohairs refers to truncated nanofibers. Truncation can be performed by using sonication at different intensity and time duration to produce nanohairs of various length including between the original length, which is typically several micrometers to a fraction of a micrometer.

Figure 2:
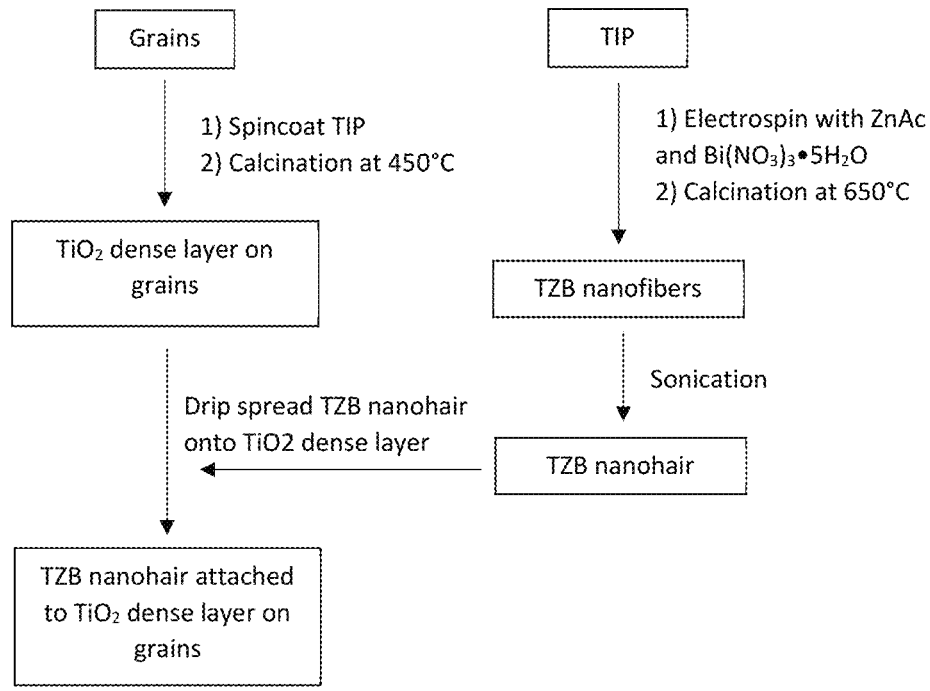
FIG. 2 shows a schematic flowchart of steps for coating of $TiO_2$—$ZnO$—$Bi_2O_3$ (TZB) nanohairs on grains (usually several millimeters to several centimeters in size) of a porous media of FIG. 1.

Referring to the flowchart depicted in FIG. 2, a 0.15M titanium iso-propoxide (TIP) ethanol solution is first spin-coated at a speed of 3000 rpm for 30 s on the surface of the porous medium. The TIP solution is then calcinated at 450° C. for 2 hours to form a TiO$_2$ adhesive layer.

TZB nanofibers are produced from electrospin of TIP with ZnAc and Bi(NO$_3$)$_3$.5H$_2$O and subsequent calcination at 650° C.

TZB nanohair is obtained following sonication of the TZB nanofibers.

Nanofibers or nanohairs suspended in ethanol can be drip coated onto the surface of the porous material containing the TiO$_2$ adhesive layer. Upon evaporation of the ethanol, these are calcinated one more time at 450° C., the nanofibers or nanohairs are attached to the TiO$_2$ adhesive layer.

Figure 3A:
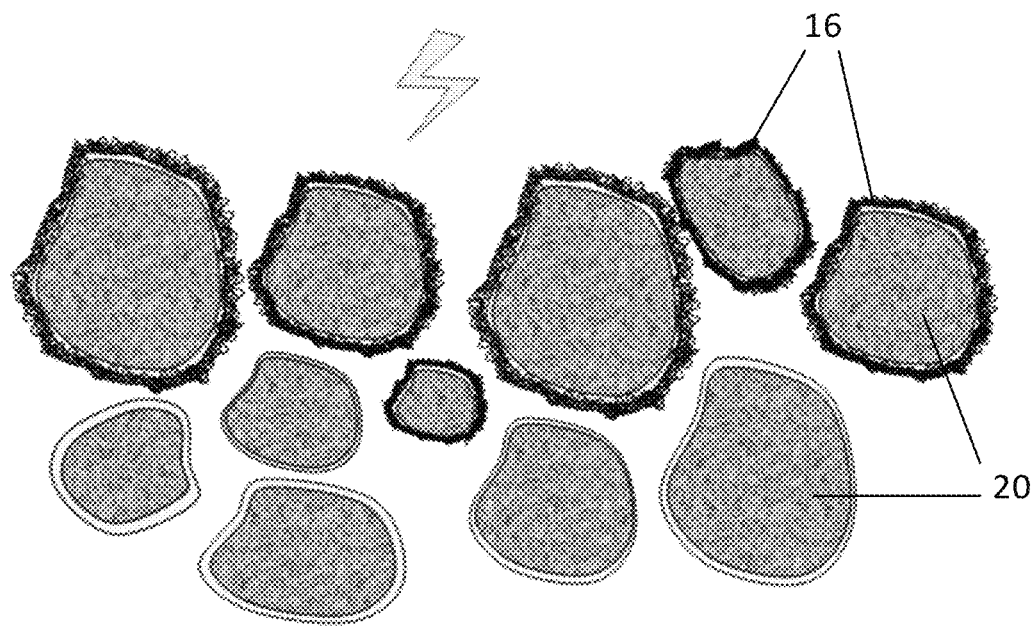
FIG. 3a shows an exemplary coating of nanofibers on grains located at the top surface of the porous media according to the method of FIGS. 1 and 2.

Generally, nanofibers are longer and these fibers may not penetrate deep into the pores of the entire surface layer of the porous material 12, which may comprise several to even tens of layers comprising grains 20 as shown in FIG. 3a. The nanofibers 16 may tend to bridge/staple across adjacent grains resisting entry inside the pores. Consequently, it is possible that only 1 to 2 layers of the grains 20 near the surface of the porous material 12 are coated with the nanofiber photocatalysts 16 as depicted in FIG. 3a.

Figure 3B:
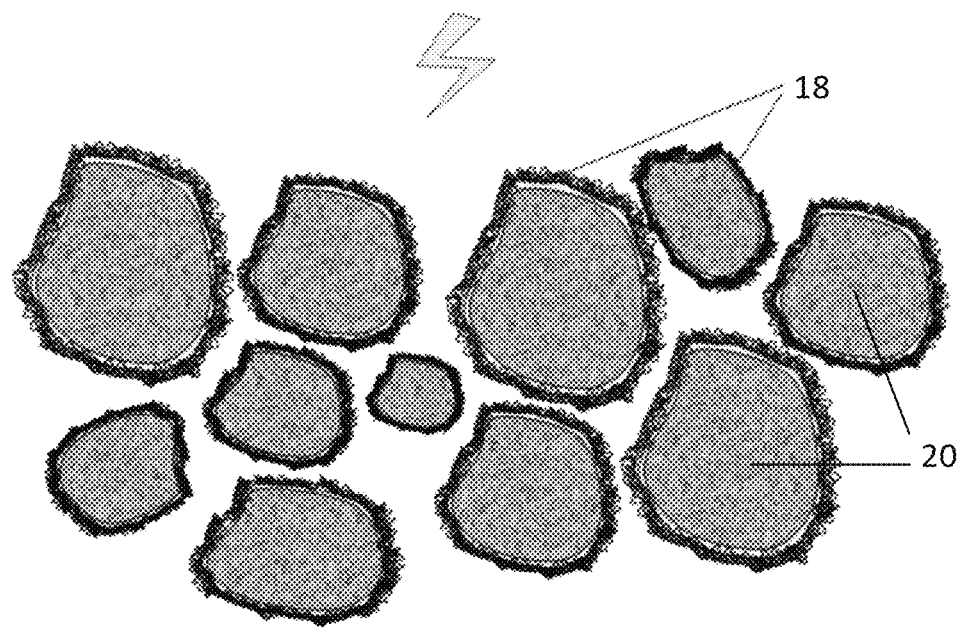
FIG. 3b shows an exemplary coating of nanohairs according to the method of FIGS. 1 and 2, wherein the coating penetrates throughout the grains across the entire depth of the porous media.

In contrast, as depicted in FIG. 3b, nanohairs 18 are smaller than the pore opening of the surface layer of the porous material 12. The nanohairs 18 can penetrate in the pores of the surface layer. Ethanol may be used as the suspension medium to carry/transport the nanohairs into the pores of the surface layer after an adhesive layer has already been coated on the surface layer. The nanohairs are left in the pores after the ethanol is evaporated. Further, after calcination at 450° C. the nanohairs will be attached to the grains 20 via the adhesive layer with deeper penetration of the photocatalysts compared with FIG. 3a.

Figure 4:
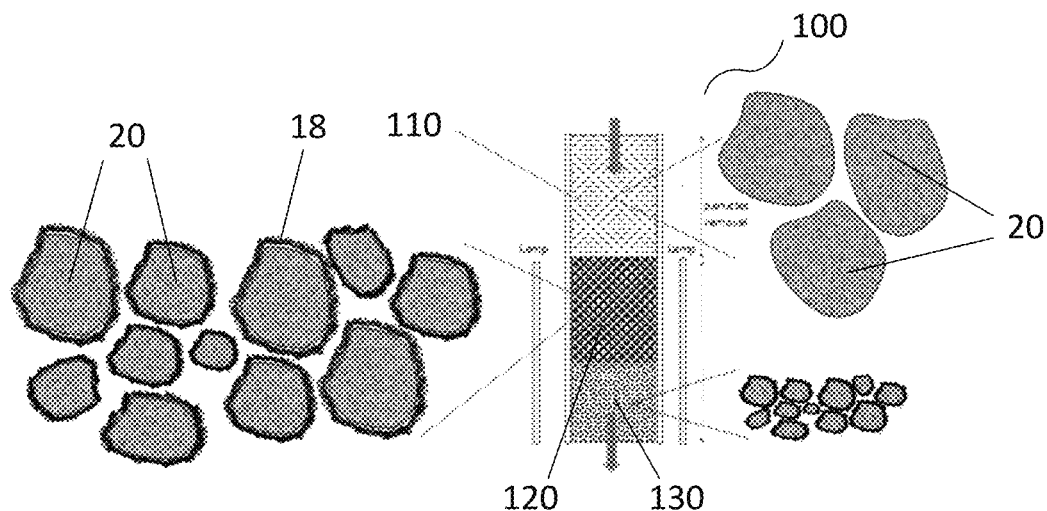
FIG. 4 shows an exemplary filtering column comprising the nanohair-coated grains of FIG. 3b.

While the setup shown in FIG. 3b allows for simultaneous filtration and photocatalytic oxidation, it would be appreciated that nanohairs 18 attached to the grain surface may be fragile and it would be preferable to carry out filtration upstream of the nanohairs which are better reserved for photocatalytic oxidation. A filtering column 100 having such setup is depicted in FIG. 4 in which a layer of porous material 110 comprising of grains 20 not coated with nanohairs 18 are placed on top of the porous material 120 comprising of grains 20 having the nanohairs 18, such that the porous material 110 on top may filter off small particles which may otherwise damage the nanohairs 18. Optionally, a further layer of porous material 130 comprising of grains of smaller size coated with nanohairs 18 may be placed between the porous material 120. The column wall in the light illumination section (i.e. where porous materials 120 and optionally 130 are located) needs to be made of transparent material (e.g. glass).

Figure 5A:
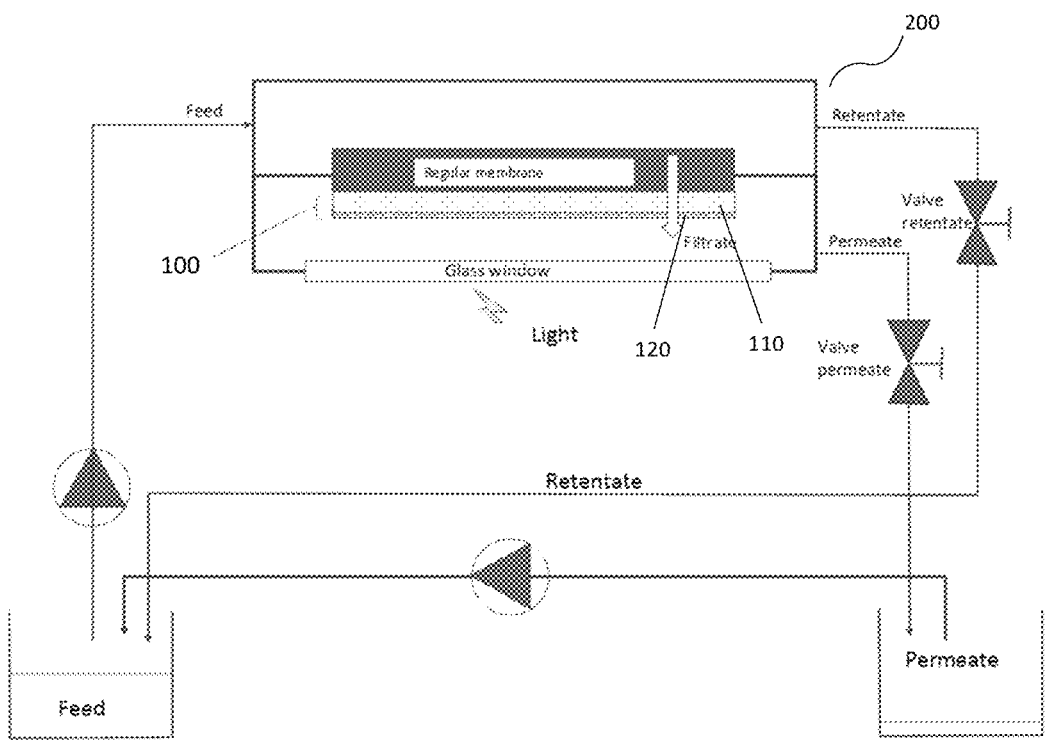
FIG. 5a shows an exemplary filter system comprising a stacked membrane purifier having the nanofiber-coated grains of FIG. 3a or 3b at the bottom of the membrane stack.

FIG. 5a shows a filtration system 200 utilizing the filtering column 100 of FIG. 4. The depicted filtration system is able to filter suspended particles in the feed (by the porous material 110 located near the inlet of the filtering column) and also oxidize organic pollutants (by the photocatalytic oxidation (PCO) effect of the nanohairs 18 attached to the porous material 120 located near the outlet of the filtering column).

Figure 5B:
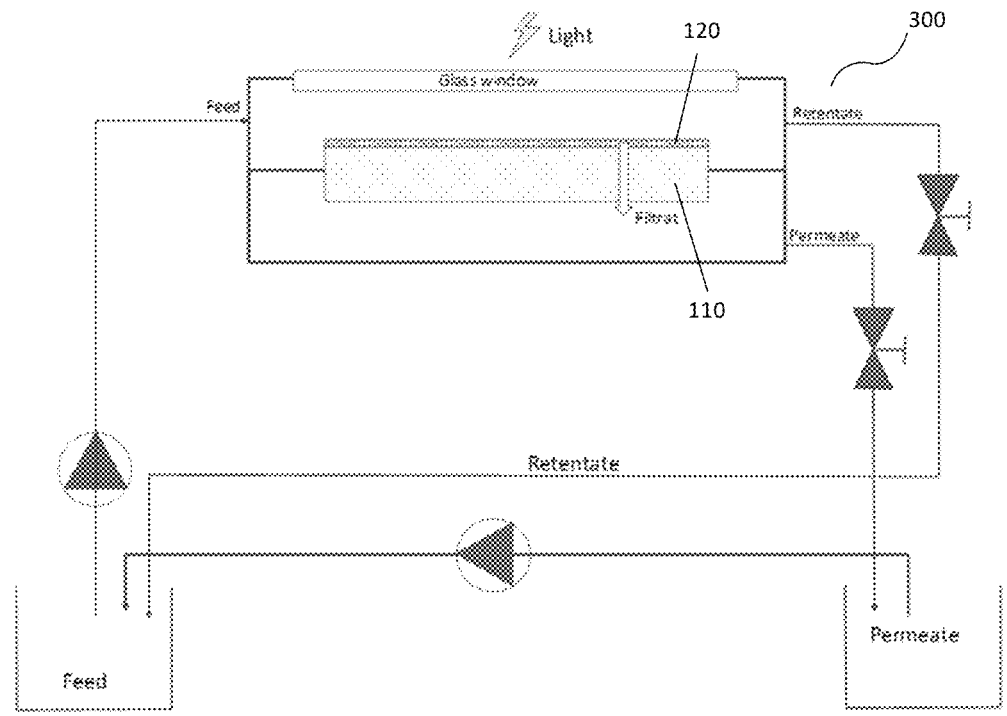
FIG. 5b shows another exemplary filter system comprising a stacked membrane purifier having the nanofiber-coated grains of FIG. 3a or 3b at the top of the membrane stack for reduction of organic foulant build up at the membrane surface.

FIG. 5b shows another filtration system 300 with a filtering column having nanohairs 18 attached grains near the inlet of the filtering column. The placing of the porous material 120 having photocatalytic nanohairs 18 on top of the filtering column are able to prevent membrane fouling from deposition of chemical complexes (organics and inorganics in nature) on the membrane surface which ultimately leads to irreversible low transmembrane flux.

Figure 6:
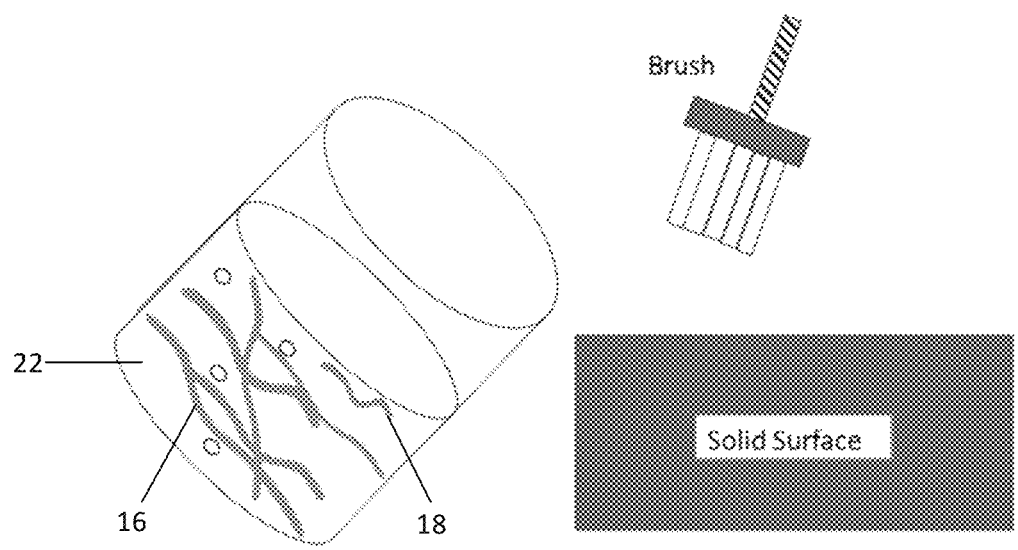
FIG. 6 shows a schematic illustration of a second aspect of the present disclosure wherein nanofibers or nanohairs dispersed in a paint suspension are applied onto a solid surface.

FIG. 6 shows a further aspect of the present disclosure wherein nanofibers 16 or nanohairs 18 are attached to a solid surface via a paint 22. The paint is preferably oil-based so that it is not soluble in water. The nanofibers and truncated nanohairs are mixed in the paint in a uniform suspension. The resulting suspension is applied to a surface in a thin layer using a paint brush 30 or similar. After drying, the paint layer forms an adhesive layer 24 (FIG. 7) which affixes the nanofibers 16 and nanohairs 18 onto the surface 32 in the region shown 34.

Preferably, the paint is white in colour. More preferably, the paint contains white pigments 26, such as pigments of calcium carbonate, kaolin or clay of small sizes (above 90% particles 1-2 micrometers) to provide the light reflecting properties for the paint (i.e. glossy paint) and/or TiO$_2$ which helps to reflect light and serves as a light scattering agent, thus trapping the light in a thin layer of painted photocatalyst and assisting oxidation of organic pollutants.

Figure 7:
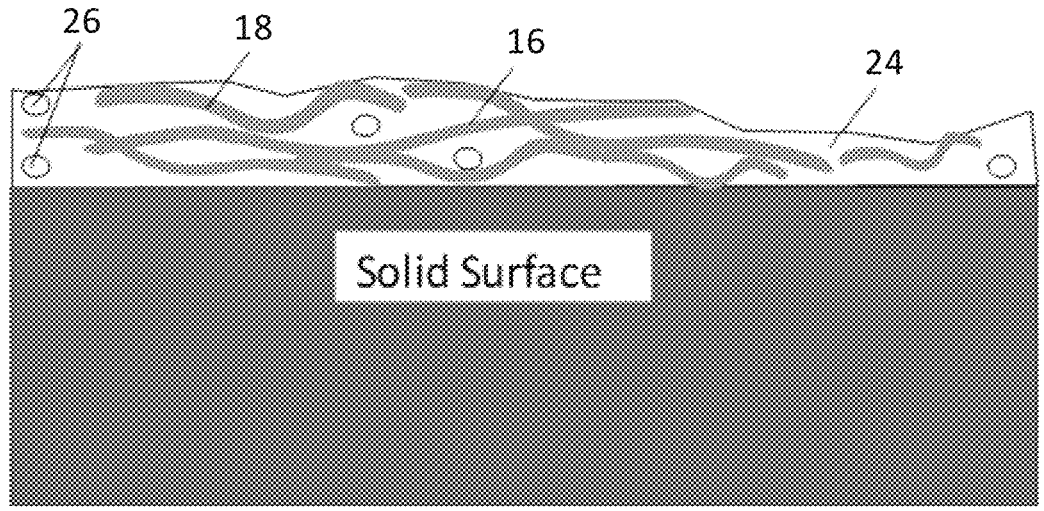
FIG. 7 shows a schematic view of an exemplary catalytic surface prepared according to the method of FIG. 6.

The affixed photocatalyst is depicted schematically in FIG. 7. The thin adhesive paint layer 24 may contain the long nanofiber and/or truncated nanohair embedded therein which is attached to the solid surface.

Figure 8:
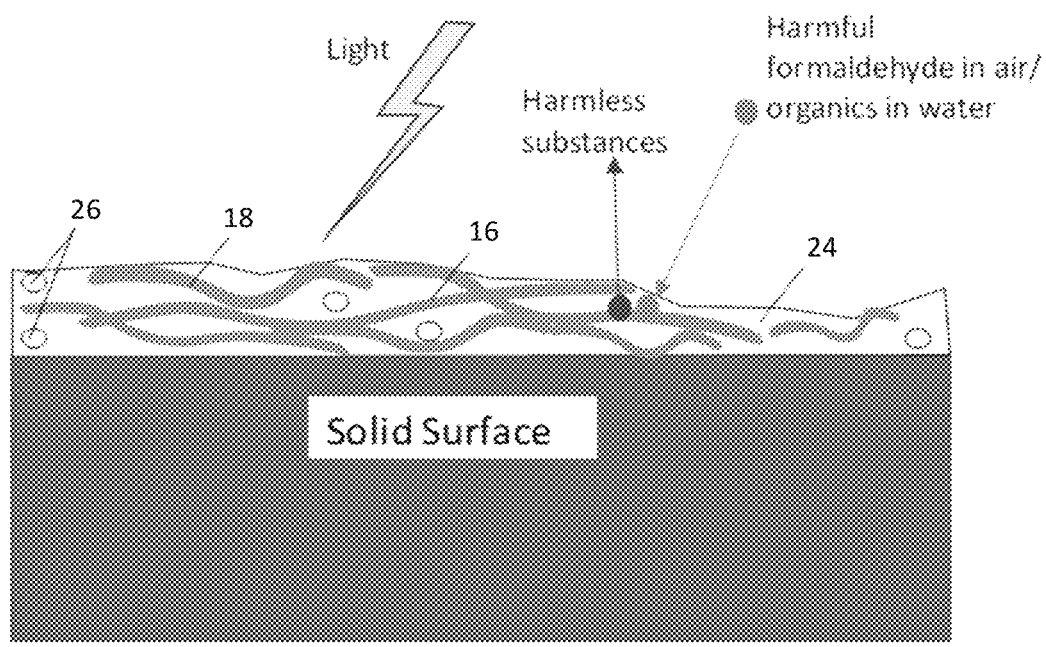
FIG. 8 shows the proposed mechanism for decomposition of pollutants by the catalytic surface of FIGS. 6 and 7.

As shown in FIG. 8, when light is incident on the surface with affixed nanofibers or nanohairs, electrons are generated and they combine with oxygen in air to form super-anions, while the holes combine with the moisture in the air to form hydroxyl radicals. Both super-anions and the hydroxyl radicals can oxidize the adhered gases molecules, bacteria or viruses that diffuse through the paint layer onto the photocatalyst surface. Once the photo-oxidation reaction (depicted by the equation below) is completed, the harmless substances such as $CO_2$ and $H_2O$ in the case of oxidation of formaldehyde are generated and they diffuse back to the air phase through the paint.

Photo-oxidation reaction of formaldehyde: $CH_2O+O_2 \rightarrow CO_2+H_2O$

FIG. 8 also illustrates an important aspect of the disclosure. The paint has to be applied in thin layers of several millimetres. Upon curing of the painted surface (with photocatalyst nanofibers), the painted layer is porous and permeable to both light and gaseous molecules, such that the gaseous molecules (oxygen, water vapour, harmful VOC and NOx molecules, etc.) can diffuse from ambient air through the porous structure of the paint layer to the underlying nanofibers (see harmful gas molecule, water vapor, oxygen molecules in air diffusing into paint layer illustrating by arrow pointing into the paint layer). The harmful gaseous molecules (NOx and VOC etc.) can adsorbed onto the surface area of the nanofibers. Light can also permeate through the pores of the paint layer to activate the photocatalyst nanofibers so that photogenerated electrons are formed to produce super-anions and hydroxyl radicals in presence of air (oxygen) and water vapor. After oxidation by the super-anions and hydroxyl radicals, harmless gases (carbon dioxide and water vapor) diffuse back to the bulk air, see arrow pointing away from paint layer. Although water vapor can penetrate through the pores of the paint, the bulk water cannot penetrate into the oil-based paint layer as the surface of the paint layer is hydrophobic. A water layer coated on the oil-based paint will break up into discrete water droplets, each having a wetting angle much larger than 90 degrees. The water droplets will roll off the painted surface (similar to water droplets rolling off a waxed car surface). Therefore, the bulk water will not enter the pores of the paint layer. Therefore, the paint layer is still impermeable to the bulk water phase despite water vapor can penetrate in the pores of the paint layer. The water vapor reacts with the positive holes (which have been separated from electrons) of the nanofiber photocatalyst to form hydroxyl radicals for oxidation of pollutant gas molecules adsorbed on the photocatalyst surface.

Figure 9:
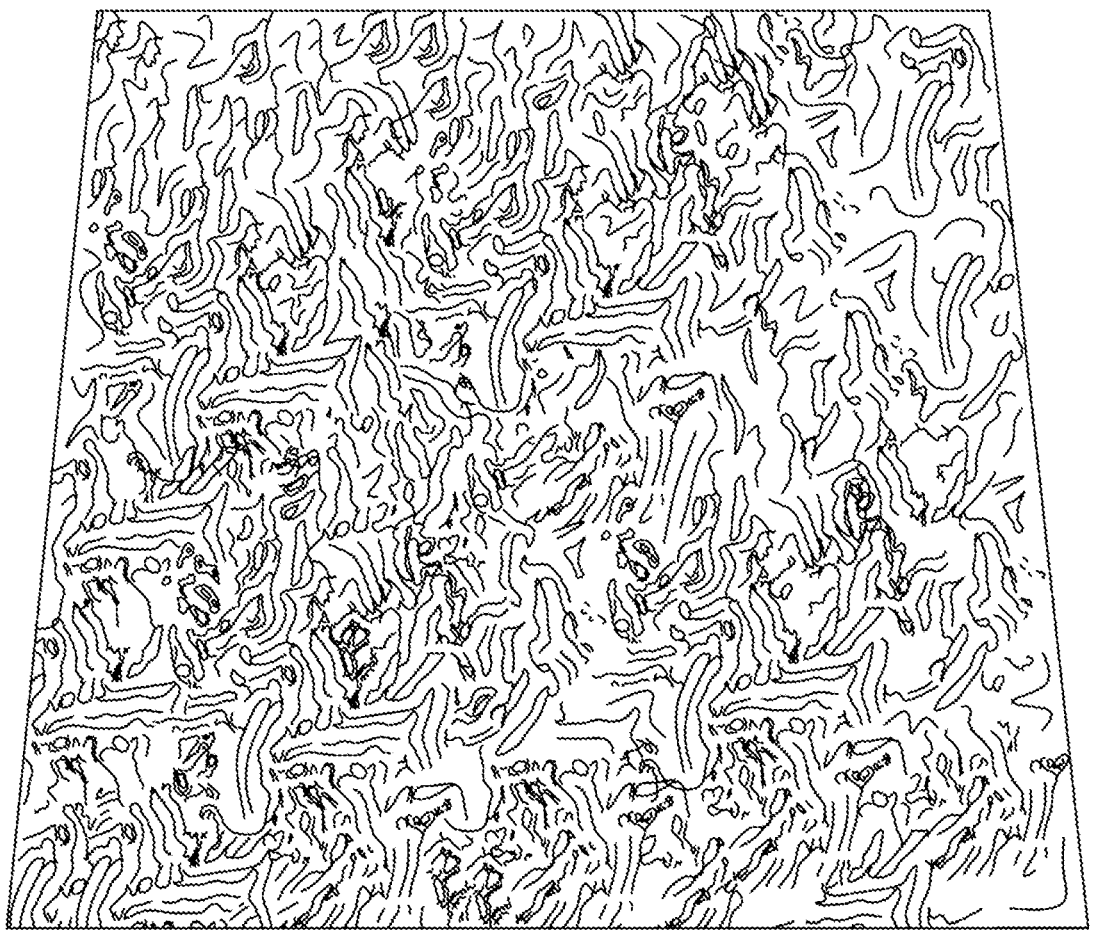
FIG. 9 shows an exemplary 7 cm×7 cm glass coated with $TiO_2$—$ZnO$—$Bi_2O_3$-Graphene (TZBG) using the method of FIG. 6.

FIG. 9 shows an exemplary glass plate (7 cm×7 cm) having TZBG nanofibers and nanohairs painted thereupon by an oil-based paint (Camel Professional Synthetic Enamel Paint, White Colour).

Figure 10A:
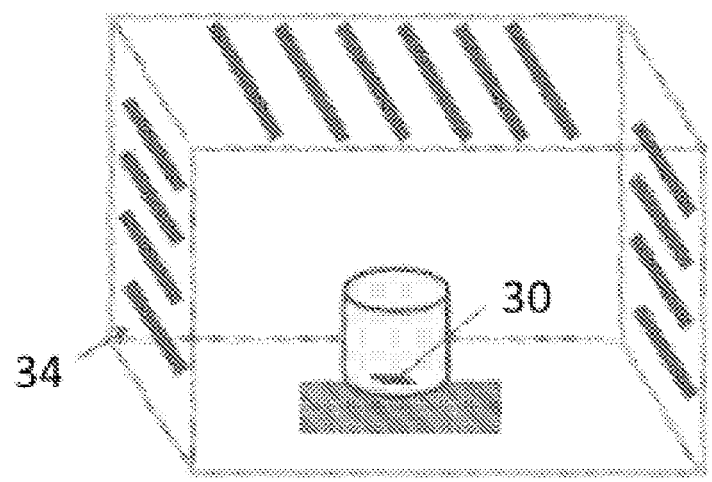
FIGS. 10a and 10b shows respectively the experimental setup for photo-catalytic oxidation using (a) photocatalyst affixed to a surface and (b) photocatalyst suspended in solution
Figure 10B:
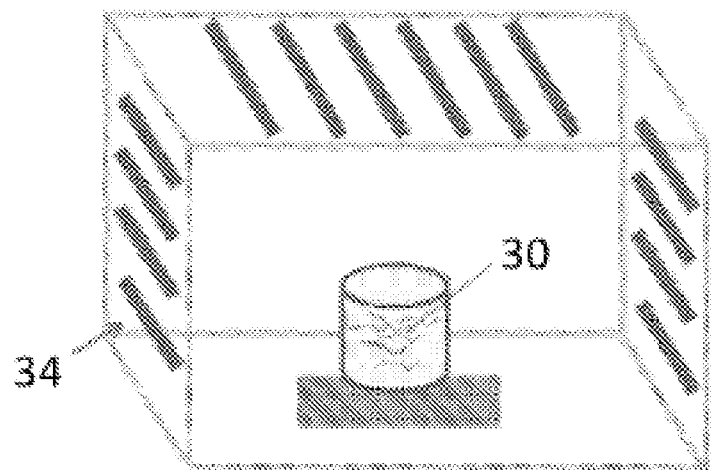

FIGS. 10a and 10b depict respectively photoreactor experiment with affixed photocatalyst 30 (on a 7 cm×7 cm glass) and photocatalyst suspended in solution 32 (control experiment). Light sources 34 of 14 VIS (Cool white fluorescent tubes) lamps (LUZCHEM LZC-4Xb photoreactor) were symmetrically placed in the LZC-4X photochemical reactor LUZCHEM (Canadian Company). The light source can be changed with lamps of different wavelength while the intensity of irradiation can be modified by rearranging the number of lamps involved in the test. A UV-Vis spectrophotometer (Agilent Technologies Cary 8454) was used to determine the concentration of Methylene Blue (MB) solutions in the beaker.

Figure 11:
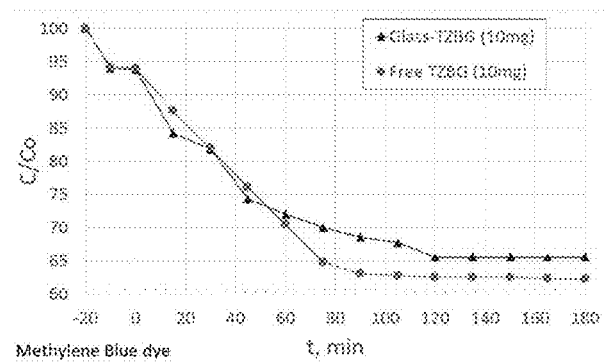
FIG. 11 shows the photo-oxidation of methylene blue in water by (a) the TZBG coated glass of FIG. 9 (with the experimental setup of FIGS. 10a) and (b) TZBG suspended in solution (with the experimental setup of FIG. 10b).

The Experiments on photocatalytic oxidation of MB were carried out with 10 mg of freely suspending or affixed TZBG photocatalyst. The results are shown in FIG. 11. C on the y-axis represents the concentration of MB and has been normalized with the maximum concentration Co (initial concentration of the dye after dark adsorption) for ease of comparison. As can be seen, the solution was first subject to dark conditions for 20 min to allow adsorption of the dye onto the photocatalyst. Subsequently, the light is turned on and the photo-oxidation process is initiated under light in which the photocatalyst breaks down the MB dye to a low level. The free 10 mg TZBG reduces the MB dye to 62.5% of the original level after 120 min reaching an equilibrium level while the affixed TZBG reduces the MB dye to 65%. The initial rate during the first 60 min is almost identical between the two.

This demonstrates that the affixed nanofibers are comparably effective as the free nanofibers in breaking down the dye or harmful organics with large molecular weight dissolved in water.

Methylene Blue (MB) dye $C_{16}H_{18}ClN_3S$ is a common test compound to simulate large harmful organics.

For the case with free TZBG, the solution was placed in a centrifuge to separate the TZBG from the liquid suspension. Subsequently, the TZBG was rinsed with distilled water to remove any remaining MB dye. This process is repeated a few times in order to recover the TZBG. In such process, some photocatalyst will be lost, however, the affixed TZBG, photocatalysts are mostly retained on the glass and can be cleaned simply by rinsing the glass plate with water for reuse.

Figure 12A:
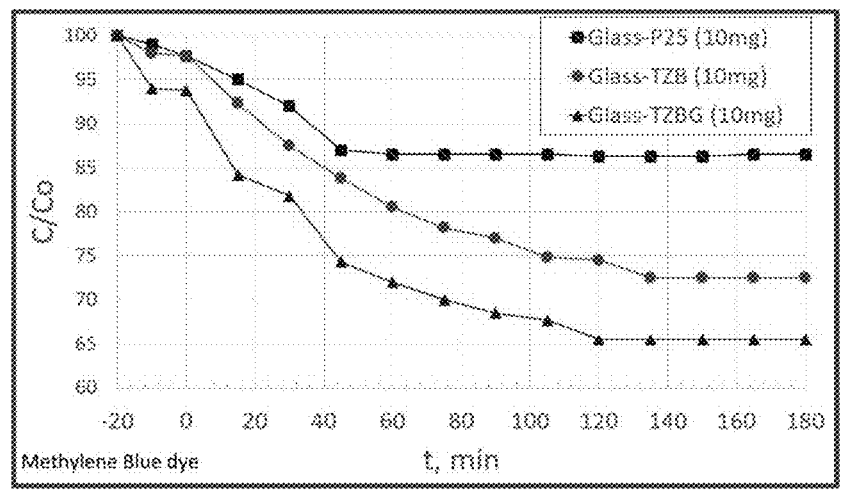
FIG. 12a shows the photo-oxidation of methylene blue in water by titanium dioxide P25 nanoparticle, TZB nanofibers and TZBG nanofibers affixed onto glass surface using the sol-gel process of FIGS. 1 and 2.

The photocatalytic effect of $TiO_2$ P25, TZB nanofibers and TZBG nanofibers affixed on 7 cm×7 cm by sol gel was studied and the results shown in FIG. 12a. 10 mg of the photocatalyst was used. The results on break-down of MB showed the catalytic activities are ranked in the order of TZBG>TZB>$TiO_2$ (P25).

Figure 12B:
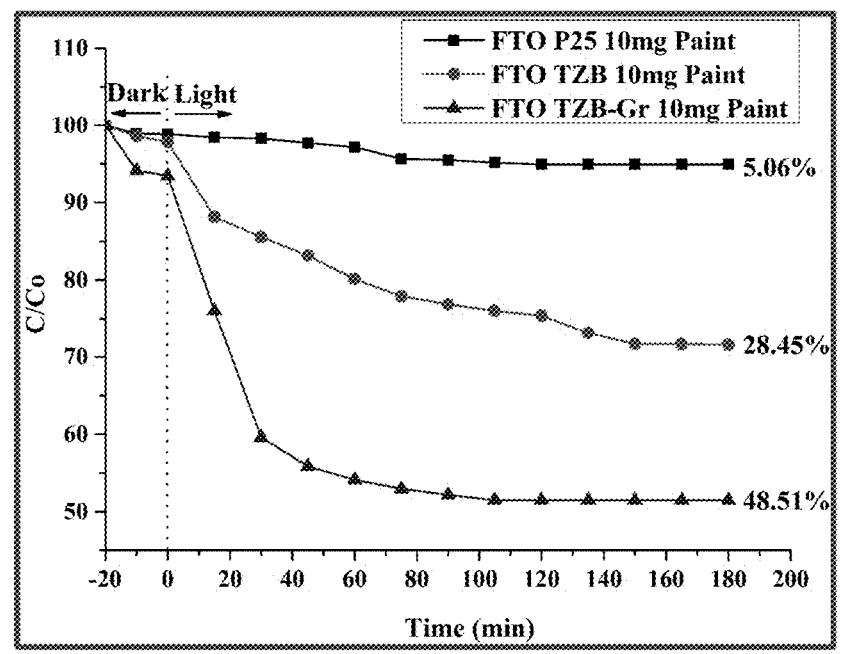
FIG. 12b shows the photo-oxidation of methylene blue in water by titanium dioxide P25 nanoparticle, TZB nanofibers and TZBG nanofibers painted onto glass surface using the paint method of FIG. 6.

The photocatalytic effect of $TiO_2$ P25, TZB nanofibers and TZBG nanofibers painted on 7 cm×7 cm was studied and the results shown in FIG. 12b. 10 mg of the photocatalyst was used. The results on break-down of MB showed the catalytic activities are ranked in the order of TZBG>TZB>$TiO_2$ (P25).

Figure 13:
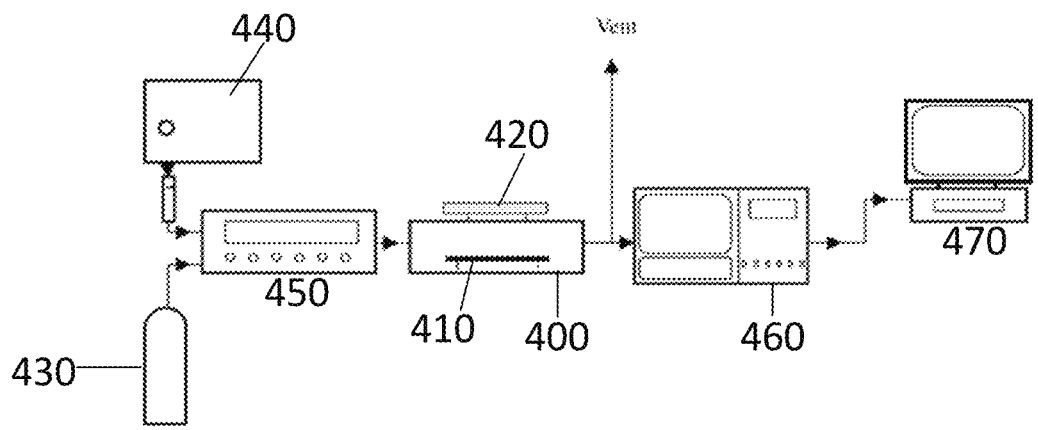
FIG. 13 shows the experimental setup for the photo-oxidation of pollutants in air which shows air of given flow rate, containing harmful test gas of known concentration, is sent to the reactor. The test gas concentration is monitored downstream of the reactor by the analyser to determine the conversion efficiency.

FIG. 13 shows an experimental setup for photocatalytic oxidation (PCO) for the removal of nitrogen monoxide (NO) in air. A continuous flow reactor 400 made of stainless steel and covered with Saint Glass at ambient temperature was used. The volume of the rectangular reactor was 4.5 L (10×30×15 $cm^3$ H×L×W). A sample dish 410 (150×25 mm) containing the catalyst nanofibers (either in the pure form or coated on glass) was placed in the centre of the reactor. A 300-W commercial tungsten halogen lamp 420 (General Electric) was used as the simulated solar light source, which was vertically positioned above the sample dish outside the reactor. The integrated ultraviolet (UV) intensity in the range of 310-400 nm was 720±10 $\mu W \times cm^{-2}$. Four mini-fans were mounted around the lamp to stabilize the temperature of the test flow system during the PCO reaction. The NO gas was introduced to the flow reactor from a compressed gas cylinder 430 at a concentration of 50.1 ppm NO (BOC) with nitrogen balance.

The initial concentration of NO was diluted to about 250 ppb by the air stream supplied by a zero air generator 440 (Thermo Environmental Inc. Model 111). The relatively humidity level of the NO flow was controlled by passing the zero air streams through a humidification chamber (not shown). The gas streams were premixed completely by a gas mixer, and the flow rate was controlled at 3 $Lmin^{-1}$ by a mass flow controller 450. The residence time was adjusted accordingly by changing the flow rate. The lamp was turned on after the adsorption-desorption equilibrium was reached among water vapor, gases, and photocatalysts. The concentration of NO was continuously measured by a chemiluminescence NO analyzer 460 (Thermo Environmental Instruments Inc. Model 42c), which can monitor NO, NO2, and NOx with a sampling rate of 0.7 L $min^{-1}$. The removal rate (%) of NO was calculated from the concentration of NO, respectively, in the feed and outlet streams and the results were recorder in a computer 470. The reaction of NO with air in the absence of photocatalyst was negligible in a control experiment, with or without light.

Figure 14A:
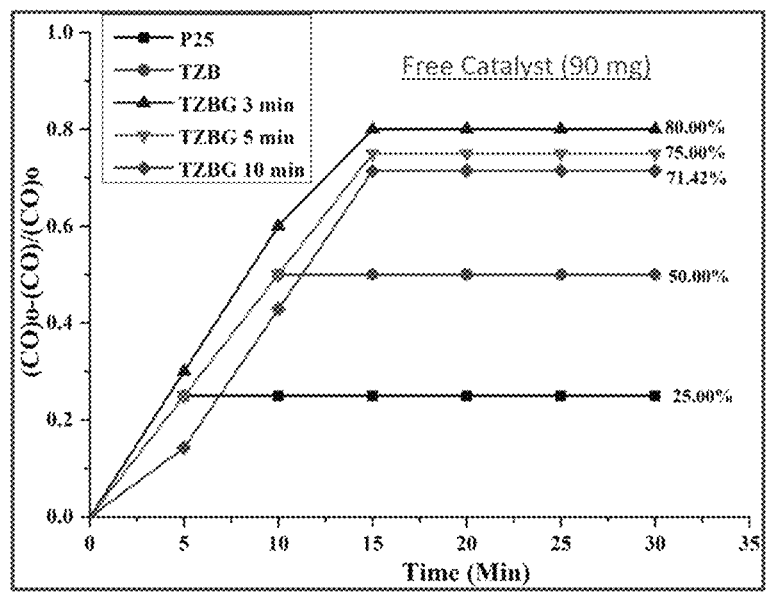
FIG. 14a shows the photo-oxidation of formaldehyde in air by 90 milligrams of free photocatalyst (i.e. not attached to any surface)—namely titanium dioxide P25 nanoparticle, TZB nanofibers and TZBG nanofibers.
Figure 14B:
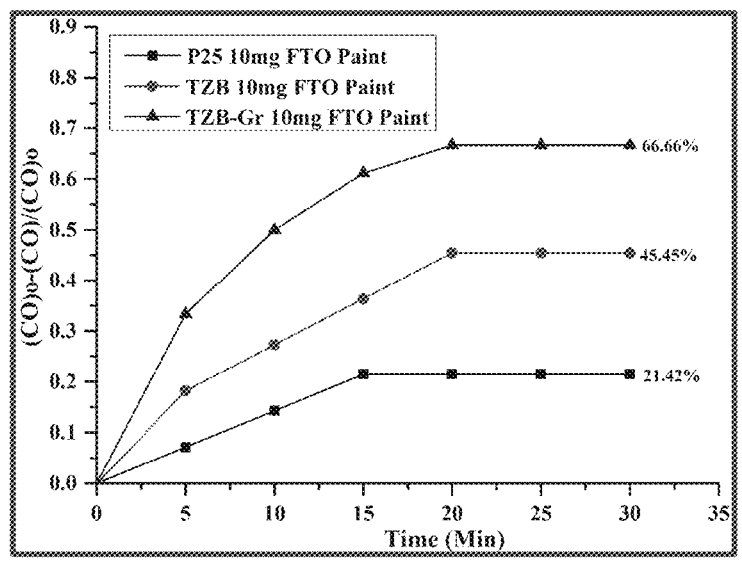
FIG. 14b shows the photo-oxidation of formaldehyde in air by 10 milligrams of titanium dioxide P25 nanoparticle, TZB nanofibers and TZBG nanofibers painted onto glass surface.

FIGS. 14a and 14b shows respectively the formaldehyde conversion by 90 milligram of the free catalyst (i.e. not affixed to any surface) (FIG. 14a) and 10 milligram of photocatalyst painted onto a 7 cm×7 cm glass plate (FIG. 14b). The results showed comparable catalytic conversion for the catalyst in its free state and when a much smaller amount of photocatalyst was affixed to a surface by an adhesive paint. However, the painted photocatalyst has the advantages that it is non-detachable, hence allows cleaning by simply rinsing the surface with water flow. It can also be used outdoor. There is no concern of nano-materials being detached and being inhaled causing health risks.

The labels TZBG 3 min, TZBG 5 min and TZBG 10 min in FIG. 14a refers to TZBG nanofibers prepared from graphene suspension that was centrifuged for respectively 3 min, 5 min and 10 min.

Figure 15:
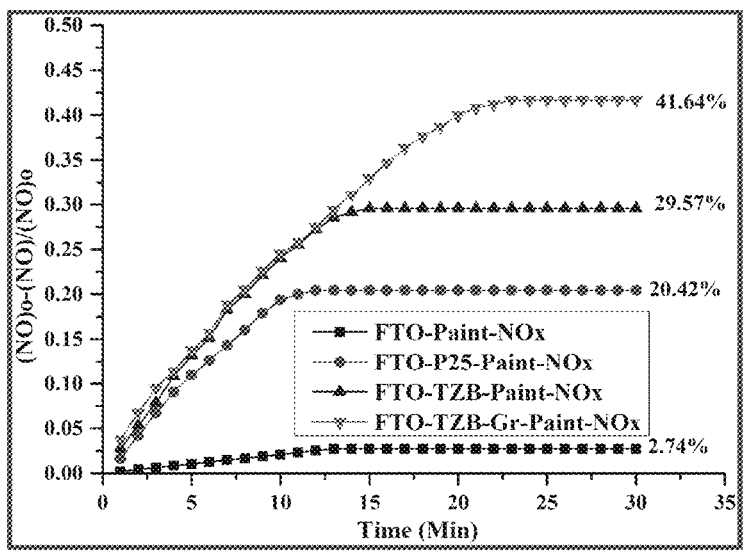
FIG. 15 shows the photo-oxidation of nitrogen monoxide in air by titanium dioxide P25 nanoparticle, TZB nanofibers and TZBG nanofibers painted onto glass surface, compared to a control painted glass surface without any nano-photocatalyst.

Similarly, FIG. 15 shows the photocatalytic oxidation of NO by painted $TiO_2$ P25, TZB and TZBG, as well as a painted surface without photocatalyst as a control. This experiment also shows the catalytic activities of these nanoparticles/nanofibers when painted on a surface. An important aspect is that the $TiO_2$, calcium carbonate and kaolin (i.e. white pigments) in the original paint (as purchased before adding photocatalyst) only provide an insignificant effect on photocatalytic oxidation of NO less than 3% as compared to 41.6% achieved with painted 10 milligrams of TZBG nanofibers. Therefore, the major function of the white pigments in the paint is to reflect and scatter the light (i.e. light trapping) than harvesting the light (serving as photocatalyst).

Figure 16:
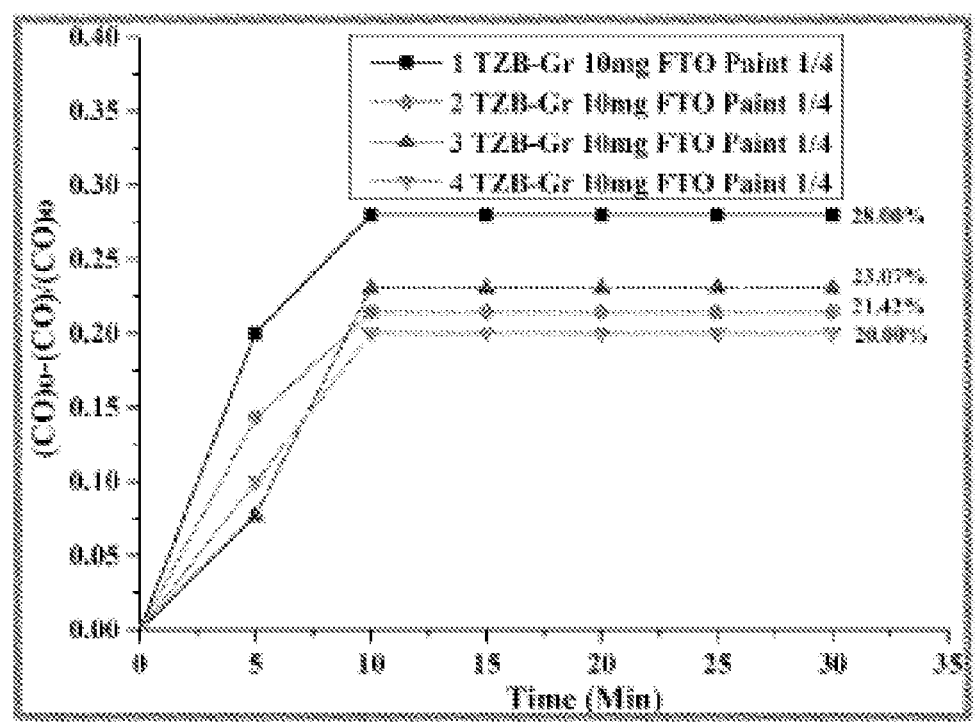
FIG. 16 shows the photo-catalytic activities of 4 equal sections (or quadrants) of the TZBG coated glass of FIG. 9.

FIG. 16 depicts the photocatalytic effect of the four quarters (upper right, upper left, lower right and lower left) of a 7 cm×7 cm glass painted with TZBG nanofiber. In each experiment, three quarters of the glass were masked by an opaque material and the photocatalytic activities of the remaining quarter was tested by passing formaldehyde through the reactor. The results indicated nearly identical or very similar catalytic activities in the four corners, suggesting an even distribution of the photocatalyst on the glass surface. This demonstrates that the application of painting the nanofibers produce a homogeneous product across the 7 cm×7 cm surface. Larger painted nanofiber photocatalyst surface can be done similarly and uniformly, which is important for practical applications.

Table 1 compares the painted photocatalyst of TZB and TZBG with the corresponding free state counterparts of TZB and TZBG, with all photocatalyst at 10 mg and at steady-state conversion (maximum conversion independent of time). The photocatalytic conversion from the paint is at 2.74%. Assuming the photocatalytic function of painted photocatalyst is equivalent to the photocatalytic function from the total contributions, i.e. from the free photocatalyst nanofibers and the paint each acting independently of each other. Thus, the sum is given by the third column of Table 1, i.e. painted TZB is 29.56% (=26.82%+2.74%), and TZBG is 39.66% (=36.92%+2.74%). However, the actual photocatalytic conversion of the painted photocatalyst for TZB is 29.57% (very close to the sum) yet the painted photocatalyst for TZBG is 41.64% which is higher than 39.66%. This demonstrates that despite the photocatalyst is shielded by the paint, the paint layer is actually porous and the shielding effect is not that strong, and the pigment particles ($TiO_2$, kaolin, calcium carbonate) in the paint help to scatter the light facilitating TZBG to further harvest the light before it escapes in the reflected light. Therefore, the performance of the painted catalyst, instead of hampered due to shielding of the paint layer, is actually higher due to the scattering of light in the paint layer that helps to trap the incident light reducing reflection or loss of the incident light. Therefore, a larger amount of finer pigments in the paint to a certain extent helps to scatter and trap light thus improving the performance of the photocatalyst.

| PC | Free | Free PC + Paint(2.74%) | Painted PC |
|---|---|---|---|
| TZBG | 36.92% | 39.66% | 41.64% |
| TZB | 26.82% | 29.56% | 29.57% |
| Paint | 2.74% | | |

PC = photocatalyst

Table 1—steady state photocatalytic conversion of TZBG and TZB, in the free state and painted Further to the above, Table 2 compares the steady-state photocatalytic oxidation of the affixed nanofibers (10 mg in all cases) using, respectively, sol-gel and paint on MB dye in water.

TABLE 2 steady-state photocatalytic oxidation performance of TiO2 P25, TZB and TZBG affixed by the sol-gel method and paint method

| PC | Free | Method 1 (sol-gel) | Method 2 (paint) |
|---|---|---|---|
| P25 | | 13% | 5% |
| TZB | | 27% | 29% |
| TZBG | 38% | 35% | 49% |

PC = photocatalyst

TiO2 P25 affixed by the sol-gel method achieves 13% conversion while painted TiO2 P25 achieves only 5% conversion. TZB achieves 27% when affixed by sol gel method and 29% if affixed by paint, which is higher. TZBG achieves 35% with sol gel while a much higher increase of 49% is achieved with the paint. An interesting comparison is that 10 mg of free TZBG only achieves 38%, which is slightly higher than the sol-gel affixed method, but much below the paint affixed method at 49%. This is distinctly related to higher performance of TZBG and the white pigments in the paint that help to scatter the light, similar to that in air application.

Preferably, nanofibers of diameter around 50-100 nm are used as photocatalysts. Despite their diameter being larger than the 25 nm diameter of $TiO_2$ nanoparticles, the surface of the nanofibers is covered with small nano-crystallites of 10 nm in size, which significantly increases the surface area of the nanofibers to an extent that is comparable to that of the $TiO_2$ nanoparticles, which has a surface area about 40-42 $m^2$/gram.

A small amount of zinc oxide and bismuth oxide is optionally added to the nanofibers such that the resultant $TiO_2$—ZnO—$Bi_2O_3$ photocatalyst can also harvest visible light. The UV and visible light take up 50% of the light spectrum, therefore the light harvesting can be increased up to 10 times compared with $TiO_2$ which only absorbs in the UV range.

The nanofibers may be provided in non-woven format, in which each fiber is adhered to other fibers at multiple points. Therefore, it is difficult for a loose fibre to detach from the nanofiber mat; unlike the case of a detached nanoparticle of $TiO_2$ from the group or cluster of particles left dried up on the surface of a wall, floor, or ceiling in the room. The present disclosure provides nanofibers and nanohairs that are affixed on a surface, such that the surface can be cleaned or sustain being wet, from washing indoor, or rain if the surface is installed outdoor, without loss of the nanofibers/nanohairs. This reduces the need for periodically replenishing the nanofiber photocatalyst for maintaining the air/water purification or disinfection function. In addition, the risks that nanomaterials are lost to the surrounding or users inhaling nano-materials are minimized.

The adhesive layer in the present disclosure is suitable for affixing nanofibers and nanohairs onto various surface, whether rigid or flexible, porous or non-permeable. The present disclosure method of affixation is suitable for attaching nanofibers and nanohairs onto even clothes, walls and any surface. There is no reason why paint, especially white paint, or similar cannot be painted on a wearable surface, i.e. clothes such as shirts and pants. The painted shirts and pants can still allow air and water vapour to percolate through the pores of the painted surface and the woven backing materials.

A white paint may be used for painting the nanofibers or nanohairs on a surface. The pigments in the white paint which has a small amount of $TiO_2$ and small sized (several micrometers) calcium carbonate and kaolin/clay particles which help to scatter the incident light in the paint layer allowing the photocatalyst to capture the light more effectively before the light gets reflected, or transmitted, from the surface.

A prototype air purifier has been built in accordance with the foregoing disclosure. In the prototype, the photo-catalytic section of the purifier has dimensions with length 30 cm, width 16 cm and height 10 cm. The walls are lined with reflective thin-gauge sheet metal for reflecting light inside the box with exception of the top which is formed from a transparent ceiling Plexiglas window 30 cm long×16 cm wide.

A 100-watt Phillips LED light is placed on the transparent top of the photo-catalytic section to provide the light source for the photocatalyst in the box. Eight (8) 7 cm×7 cm glass tiles painted with TZBG photocatalyst similar to that depicted in FIG. 9 were placed on the bottom of the photo-catalytic section. It would be appreciated that the dimensions of the purifier are sized according to the number of tiles to be included.

Air with formaldehyde and other organic compound is first filtered using a microfiber filter at the entrance of the purifier to remove particles and subsequently air with harmful test gas flow through the photo-catalytic section where the harmful gas is converted to harmless substances.

Figure 17A:
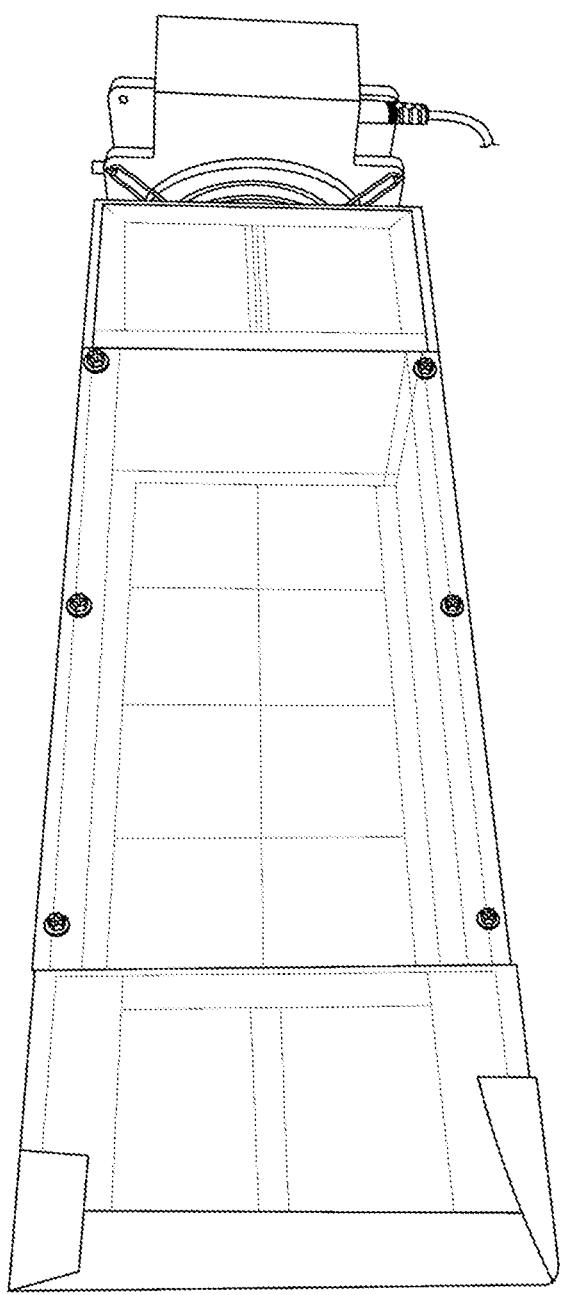
FIG. 17a shows a prototype air purifier showing 8 tiles as depicted in FIG. 9 coated with photocatalyst lining the base of the photocatalytic region.
Figure 17B:
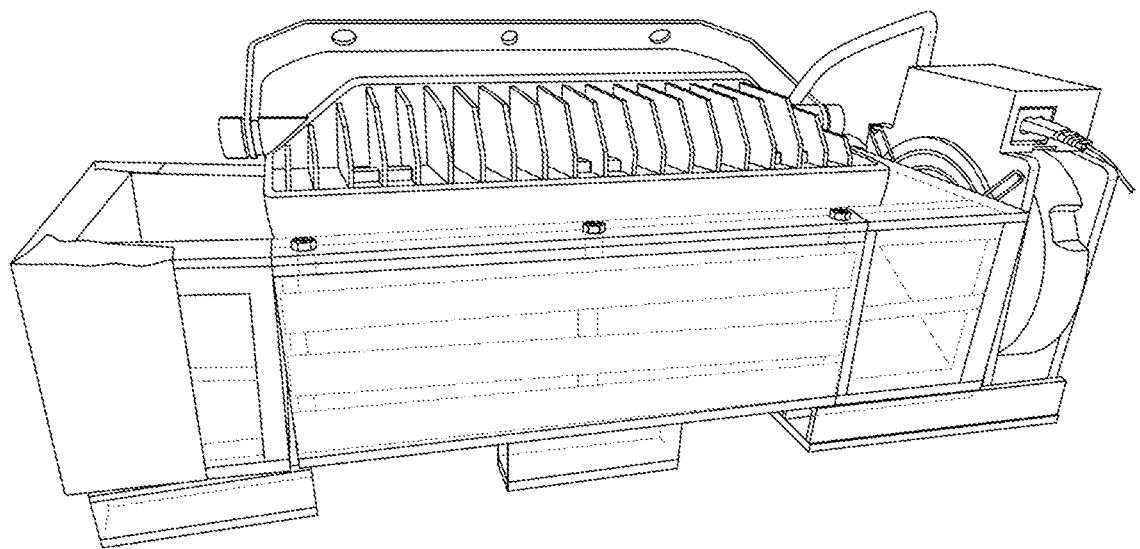
FIG. 17b shows the exemplary prototype air purifier of FIG. 17a including a 100 w LED light placed thereon.

Air was drawn through the purifier by a suction fan with variable speed to provide uniform air flow through the photo-catalytic section of the purifier. A photograph of the prototype air purifier is shown in FIG. 17a without the light; exposing the photo-catalytic section and in FIG. 17b with the light on top of the photo-catalytic section.

The purifier is placed in a "test box" with dimensions of 45 cm by 45 cm cross-section and 74 cm in length enclosed at both ends.

The test box was sprayed with aerosol lacquer black paint so that the initial test box is filled with formaldehyde at initial concentrations of respectively, 370 ppb (parts per billion), 160 ppb, 290 ppb, and 360 ppb as measured by a portable formaldehyde meter placed inside the box.

Subsequently, the concentration of the formaldehyde is measured every 5 minutes until the level drops to a low level.

Figure 18A:
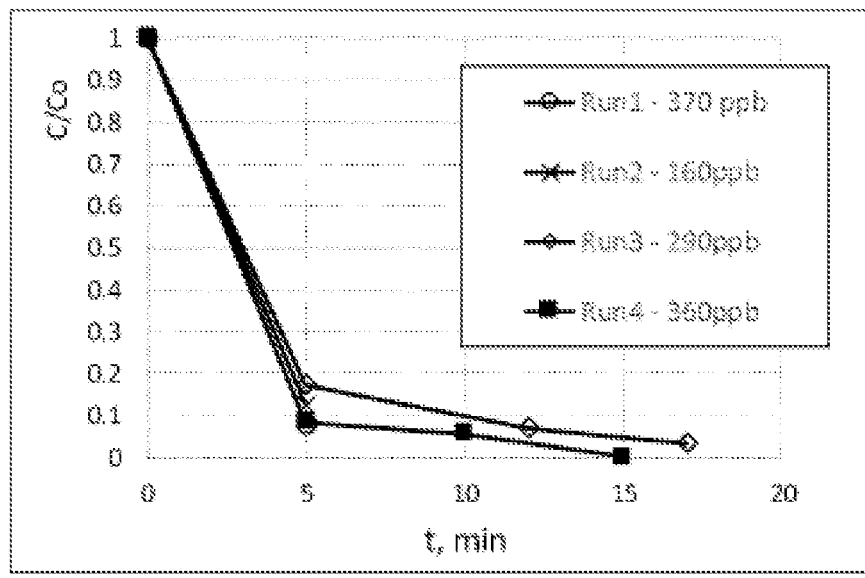
FIG. 18a shows the ratio of formaldehyde concentration of the air purifier of FIG. 17a normalized to initial concentrations for various initial concentrations.

The ratio of the concentration to the initial concentration of the 4 test runs is shown in FIG. 18a. As shown in FIG. 18a, after 5 minutes, the formaldehyde irrespective of initial concentration plunges down to 10% of its original level, and within 15 minutes, it dropped to a few percent of its initial level. It is noted in one run the formaldehyde reached an undetectable level.

Figure 18B:
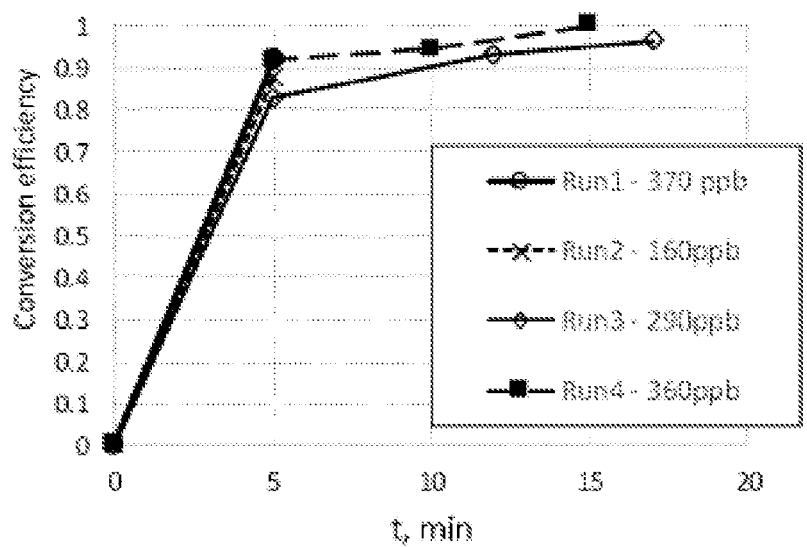
FIG. 18b shows the conversion efficiency of formaldehyde by the air purifier of FIG. 17a for various initial concentrations.

The results are shown in FIG. 18b in terms of conversion efficiency, and the conversion efficiency of breaking down formaldehyde to harmless substances is very high in the 90% range in the first 5 minutes. This is similar in behavior as FIGS. 14a, 14b and 16 for the formaldehyde tests as described herein. The prototype has demonstrated that it can purify formaldehyde at initial high concentration of 300-400 ppb down to residual level of 10-20 ppb concentration at a rate of 15 liter per minute. These results demonstrate the effectiveness of the present invention in air purification.

The above embodiments are described by way of example only. Many variations are possible without departing from the scope of the invention as defined in the appended claims.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

The invention claimed is:

1. A surface comprising a photocatalyst comprising TiO2-ZnO, TiO2-Bi2O3, TiO2-CuO, TiO2-CuO-Gr, TiO2-ZnO—Bi2O3 or TiO2-ZnO—Bi2O3-Gr, nanofiber or nanohair affixed thereupon and dispersed within an adhesive layer comprising an oil based alkyd resin paint.

2. The surface of claim 1, wherein the photocatalyst comprises TiO2, TiO2-ZnO, TiO2-Bi2O3, TiO2-CuO, TiO2-CuO-Gr, TiO2-ZnO—Bi2O3 or TiO2-ZnO—Bi2O3-Gr.

3. The surface of claim 1, wherein the photocatalyst is TiO2-ZnO—Bi2O3-Gr nanofiber or nanohair.

4. The surface of claim 1, wherein the oil-based paint comprises a white pigment.

5. The surface of claim 4, wherein the white pigment is calcium carbonate, kaolin or titanium dioxide.

6. The surface of claim 1, wherein the adhesive layer is permeable to light and gas.

7. The surface of claim 1, wherein the photocatalyst is affixed via thermal treatment of an adhesive layer having the photocatalyst thereupon.

8. A method of affixing a photocatalyst to a surface comprising applying a suspension of the photocatalyst in an oil-based alkyd resin paint to the surface, wherein the photocatalyst comprises TiO2-ZnO, TiO2-Bi2O3, TiO2-CuO, TiO2-CuO-Gr, TiO2-ZnO—Bi2O3 or TiO2-ZnO—Bi2O3-Gr nanofiber or nanohair.

9. The method of claim 8, wherein the photocatalyst is consists of TiO2-ZnO, TiO2-Bi2O3, TiO2-CuO, TiO2-CuO-Gr, TiO2-ZnO—Bi2O3 or TiO2-ZnO—Bi2O3-Gr nanofiber or nanohair.

10. The method of claim 8, wherein the photocatalyst is TiO2-ZnO—Bi2O3-Gr nanofiber or nanohair.

11. The method of claim 8, wherein the oil-based paint comprises a white pigment.

12. The method of claim 8, wherein the white pigment is calcium carbonate, kaolin or titanium dioxide.

13. A purifier comprising a photocatalyst comprising TiO2-ZnO, TiO2-Bi2O3, TiO2-CuO, TiO2-CuO-Gr, TiO2-ZnO—Bi2O3 or TiO2-ZnO—Bi2O3-Gr nanofiber or nanohair, wherein said photocatalyst is dispersed in and affixed on a surface via an adhesive layer wherein the adhesive layer comprises TiO2 and an oil based alkyd resin paint.

14. The purifier of claim 13, wherein the adhesive layer has a composition substantially the same as the photocatalyst.

15. The purifier of claim 13, wherein the adhesive layer has a composition at least 50% similar with the photocatalyst.

16. The purifier of claim 13, wherein the photocatalyst is TiO2-ZnO—Bi2O3-Gr nanofiber or nanohair.

17. The purifier of claim 13, wherein the adhesive layer is permeable to gas and water vapor.

18. A purifier system comprising
an inlet in fluid communication with an outlet,
the purifier of claim 13 disposed on a fluid path from the inlet to the outlet.

19. The purifier system of claim 18, wherein the photocatalyst is affixed proximal to the intake surface or output surface of the fluid path or along any surface of the fluid path.

\* \* \* \* \*